United States Patent [19]

Fischer

[11] 4,416,724

[45] Nov. 22, 1983

[54] METHOD FOR PRODUCING INSULATOR SURFACES

[75] Inventor: Bernd Fischer, Ober-Ramstadt, Fed. Rep. of Germany

[73] Assignee: Gesellschaft für Schwerionenforschung mbH, Darmstadt, Fed. Rep. of Germany

[21] Appl. No.: 329,205

[22] Filed: Dec. 9, 1981

[30] Foreign Application Priority Data

Dec. 11, 1980 [DE] Fed. Rep. of Germany ....... 3046629

[51] Int. Cl.[3] ........................ B44C 1/22; C03C 15/00; A61K 27/02; A61N 5/00

[52] U.S. Cl. .................................... 156/628; 156/633; 156/643; 156/654; 156/668; 156/213; 250/472.1; 250/473.1; 250/492.3

[58] Field of Search ............... 250/472.1, 473.1, 492.1, 250/492.3; 156/625, 628, 629, 633, 643, 654, 668, 145, 209, 219, 213

[56] References Cited

U.S. PATENT DOCUMENTS 4,268,347 5/1981 Stephens ............................ 156/628

*Primary Examiner*—William A. Powell

*Attorney, Agent, or Firm*—Spencer & Frank

[57] ABSTRACT

A method for producing insulator surfaces by increasing the surface area of a solid body presenting such surface, which method is carried out by uniformly bombarding the surface of the body with a collimated beam of ions generating latent nuclear tracks in the surface, and etching the bombarded surface to widen the nuclear tracks into adjacent, individual etched channels at least some of which contact one another.

4 Claims, 2 Drawing Figures

METHOD FOR PRODUCING INSULATOR SURFACES

BACKGROUND OF THE INVENTION

The present invention relates to a method and apparatus for increasing the surface area of insulator bodies.

The insulating properties of insulating bodies are frequently lost or materially reduced because their surfaces become contaminated by conductive deposits. This may be caused by metal vapors, for instance, which are deposited on an insulating body when sparkovers occur or during the operation of metallic-ion sources.

Attempts have been made to improve the insulating properties of insulators by increasing their surface area. To this end, a specialized shaping of the insulating body is used, e.g., the surface area may be increased by means of surface embossments or ribs. The insulating properties are then supposed to worsen only after there has been relatively extensive contamination by conductive deposits on the increased insulator surface.

However, the increase in surface area attainable by such shaping is rather small, i.e., by a factor of 10 or less, so that only limited protective effects are attained.

SUMMARY OF THE INVENTION

It is accordingly an object of the present invention to improve the insulating properties of insulators, and particularly of those insulators exposed to deposits of metal vapors, such as occur during sparkovers or during use in sputter ion sources, by greatly increasing their surface area.

In order to attain this object, the present invention proposes a method in which the insulator surface is uniformly bombarded with a collimated beam of ions which generate a myriad of minute nuclear tracks in the insulator surface. These latent tracks are then enlarged and widened by a known etching medium, such that adjacent, individual etched channels intersect or touch one another. The beam should particularly advantageously be made up of heavy ions. One advantageous use of the invention results from the formation of a bombarded and etched foil in which existing insulator structures can be enveloped in such a manner that their original shape is retained. Preferably, the insulator surface porosity attained by the method is approximately 1; where the porosity is defined as the quotient of the product of the number of channels and the surface area of the individual channels over the total surface area of the unprocessed material.

In a particularly advantageous apparatus proposed by the invention for performing the method according to the invention, the energy, density and ionic type of the heavy-ion beam are specified in accordance with the depth of the structuring to be effected and with the material to be bombarded; a heavy-ion accelerator is used to generate the heavy-ion beam, with a vacuum chamber which is entered by the beam and in which the apparatus itself is located. The apparatus comprises a grid, which rotates transversely relative to the beam and is disposed ahead of the solid-state matrix to be bombarded (as viewed in the direction of beam travel), and a magnetic deflector traversed by the beam before it passes to the sample or the apparatus holding the sample.

By utilizing the method of the present invention, it is possible to increase the insulating body surface area, or that of its solid-state matrix, by a factor of 1000 or more, which cannot be achieved by conventional methods. This substantially increases the protective effect attained.

The method according to the invention furthermore enables the production of either an insulating body or a foil which is structured according to the method and then wound about the insulating body to attain the desired protective effect. The utilization of the method is independent of the shape of the insulating body, and this shape can be determined by other technical considerations, such as mechanical strength, weight, or a shape which can be fabricated simply and at a favorable cost. The protection of the surface is attained by means of a microscopic structuring of the surface which can be formed on any macroscopic structure.

Where a protective foil, produced in accordance with the method of the invention, is used, this foil can be fabricated, using state-of-the-art accelerator technology, at a rate of approximately one square meter of foil surface per second. Thus, a wide range of problems can be solved at a favorable cost, using a standard product.

Finally, a further advantage of the present invention is that the microstructure produced in accordance with the method also suppresses the emission of secondary electrons and ions and of ultraviolet light, thus substantially eliminating a further source for the dissemination of high-voltage sparkovers.

DESCRIPTION OF THE PREFERRED EMBODIMENTS

Figure 1:
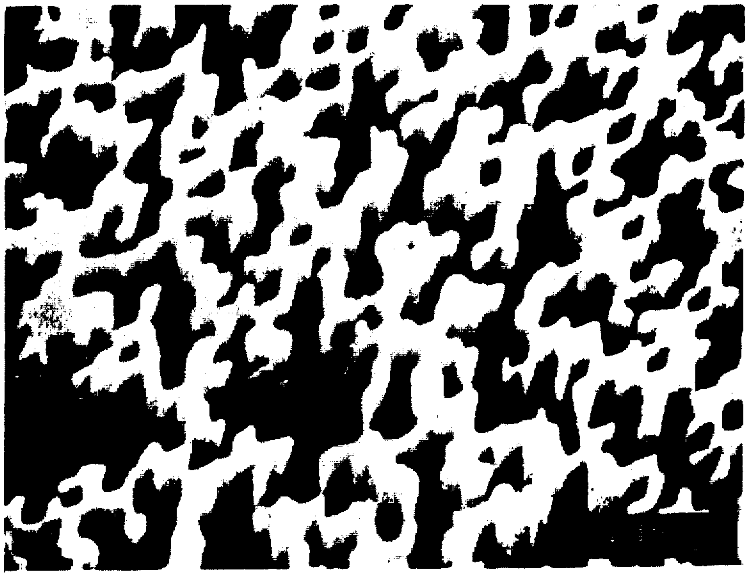
FIG. 1 is a scanning-electron micrograph of an insulator surface produced in accordance with the invention.

In FIG. 1, one example of a mica surface, structured in accordance with the described method, is shown. The illustration is an original scanning-electron microscope photograph incorporating a scale for reference purposes. In order to be able to make this structure at least very slightly conductive in order to make the scanning-electron micrograph, it was fabricated with a dosage of approximately $10^9$ ions/cm$^2$ and with particularly wide etched channels. Actually, the optimal porosity would be approximately 1, this porosity being expressed as $$P = \frac{\text{number of holes} \times \text{surface area of individual channel}}{\text{total surface area of non-etched material}}$$

The surface area of the individual channel is the average surface area of a channel created by the etching, or the opening of an individual etching channel on an unimpaired or large surface. The porosity P may be either greater than or less than 1. It is greater than 1 if there is "over-etching"; that is, if the structuring is relatively extensive. The rhomboid shape of the channels shown in FIG. 1, where the porosity P has been selected as greater than 1 for photographic reasons, is dictated by the crystalline structure of mica and by the hydrofluoric acid used as the etching acid; it is not critical to the attainment of the desired effect.

The insulating body to be treated is bombarded in a vacuum with a beam of heavy ions. Latent nuclear track channels are thus formed, with a diameter of approximately 100 Å and a depth which is dependent on the ionic energy and may be, for instance, 10μ for an ionic energy of approximately 1 MeV/nucleon. These channels are widened by a subsequent developing or etching process to a larger diameter of arbitrary dimension. By appropriately selecting the bombardment dosage (number of ions per $cm^2$) and the development time for the appropriate etching medium, approximately half of the surface of the insulating body or solid-state matrix is covered with etched channels, so that a labyrinthine surface structure is the result.

The protective effect attained with the method is shown by the following comparative examples:

EXAMPLE 1

An untreated mica chip was coated with gold in a sputter system at a 20 mA discharge current for 4 minutes.

EXAMPLE 2

Figure 2:
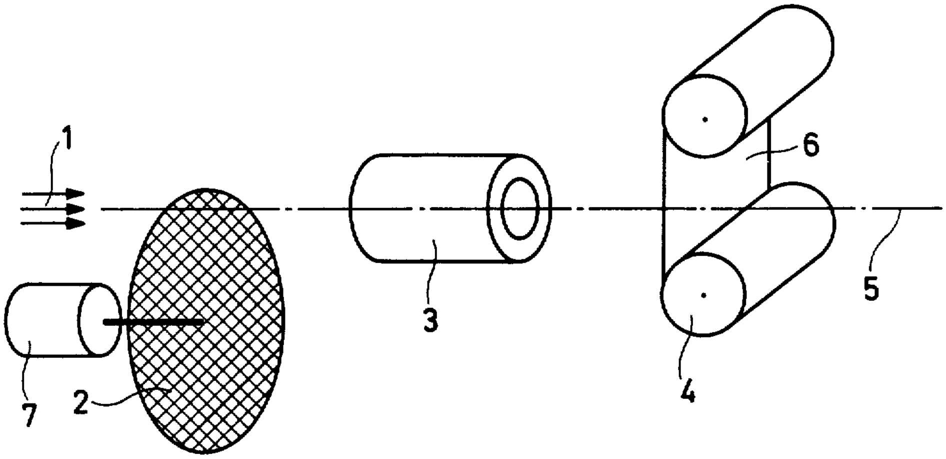
FIG. 2 is a schematic perspective view of an embodiment of apparatus according to the present invention capable of carrying out the method.

An identical mica chip was bombarded with approximately $5\times10^8$ of 1.4 MeV/nucleon argon ions per square centimeter, utilizing the apparatus illustrated in FIG. 2. The bombarded chip was then etched by being placed for 20 minutes in a 40% aqueous solution of hydrofluoric acid. The bombarded and etched chip was then coated with gold, as described in Example 1.

The insulation resistance of each of the chips was then measured at a test voltage of 1 KV. The resistance of the chip of Example 1 was about 50Ω, the resistance of the chip of Example 2, conforming to the invention, was in excess of $1\times10^{10}$Ω.

Instead of a solid body of relatively large volume, it is also possible to structure a flat insulating foil or insulating sheet with the method in such a way that its insulating properties are greatly improved. With this foil, which can be fabricated simply and in large quantities, it is then possible to protect any known insulating body against metal vapors by wrapping it in the foil. The foil can be selected in such a manner that it has particularly favorable properties in terms of the registration of nuclear tracks and chemically developing them. Materials which are particularly favorable are those in which it is possible to create etched nuclear tracks whose diameter is as constant as possible. However, in principle, latent nuclear tracks can be created in all insulating solid bodies and then widened by etching to form more or less narrow conical channels.

FIG. 2 is a schematic illustration of a bombardment apparatus for the proposed method, which is located in a vacuum at a pressure of less than $10^{-4}$ Torr. The heavy-ion beam 1 extends along the axis 5 and within the vacuum housing, not shown in detial. The heavy-ion beam 1,5 is generated by a heavy-ion accelerator—in this case, preferably of the UNILAC type—and directed into the vacuum chamber where bombardment takes place. Its energy and ionic type are selected beforehand in accordance with the depth of the structuring to be effected and with the type of material to be bombarded. A grid 2 rotating in the beam 1 intercepts a portion of the beam and is utilized for measuring the dosage. The grid is driven by the motor 7.

An annular, tubular magnetic deflector 3 is introduced into the beam 1 following the grid 2 and is placed centrally relative to the axis 5 of the beam. With the aid of the magnetic deflector 3, the beam 1 is spread, or deflected, so as to be capable of exposing a larger surface area 6 of the solid body or sample to be bombarded to uniform bombardment at the desired density. The holder 4 for the material to be bombarded is disposed following the deflector 3, which may be annular in form.

In the illustrated form of embodiment of the holder 4, it is composed of two conveyor rollers, between which a foil-like solid-state matrix, constituting the surface 6 to be bombarded, can be advanced while traversing the beam axis 5. The bombardment dosage can be adjusted by adjusting the winding speed. Where an insulating body that is three-dimensional in shape rather than flat is to be bombarded, it can be supported on a rotating platform or the like, so that all sides of the insulating body can be bombarded.

After the insulator has been bombarded, whether it is a three-dimensioned body or a flat foil, the insulator is immersed in an etching bath to develop the improved surface of the present invention.

The deflection sweeps the beam over the foil to get a constant fluence (fluence = number of projectile ions per $cm^2$) over the area to be irradiated. This is a well proven technique in ion implantation and state of the art. The operation data of the deflector depend on the required dose which is preferably between $10^6$ and $10^{10}$ ions/$cm^2$. The kind of the ions is widely variable, preferably ions heavier than neon should be used.

There are no restrictions on foil thickness, except that it must be thicker than the depth of the insulating microstructure, which may be between 5 and 100 microns depending on the energy of the bombarding ions. It is possible to take any shape for the body or the foil.

Any insulating material may be used as far as its etching speed along a latent track is at least 10 times faster than in the unperturbed material. This applies to most plastics, e.g. polycarbonate, polymethylmethacrylate, or more generally to plastics with polymer chains of very high molecular weight.

The used term latent track is a term borrowed from photography and means that a latent track needs chemical treatment to become detectable. (Though it is visible under the transmission electron microscope).

All ions over the periodic table can be used depending on the specific material to be irradiated. But generally the heavier ones do better. The developing solution also depends on the insulator material.

It will be understood that the above description of the present invention is susceptible to various modifications, changes and adaptations, and the same are intended to be comprehended within the meaning and range of equivalents of the appended claims.

What is claimed is:

1. A method for producing insulator surfaces by increasing the surface area of a solid body constituting an electrical insulator and presenting such surface, comprising uniformly bombarding the surface of the body with a collimated beam of ions having a density of $10^6$–$10^9$ ions/$cm^2$ generating latent nuclear tracks in the surface, and etching the bombarded surface to widen the nuclear tracks into adjacent, individual etched channels in a manner to cause the number of channels multiplied by the surface area of an individual channel and divided by the total non-etched surface to be approximately equal to 1.

2. A method as defined by claim 1, wherein the beam comprises heavy ions and said step of bombarding is carried out on the basis of the composition of the body to produce latent nuclear track channels of a depth of the order of 10μ.

3. A method as defined by claim 1, wherein the solid body is a foil.

4. A method of increasing the electrical resistance of an insulator body comprising the steps of ionically bombarding substantially the entire surface of a separate insulating sheet, etching the bombarded surface, and enveloping the insulator in said sheet while retaining the shape of the insulator.

* * * * *